(12) United States Patent
Umeda et al.

(10) Patent No.: US 7,197,351 B2
(45) Date of Patent: Mar. 27, 2007

(54) PORTABLE ELECTROCARDIOGRAPH

(75) Inventors: Masahiro Umeda, Kyoto (JP); Norihito Yamamoto, Kyoto (JP); Kazuhisa Tanabe, Kyoto (JP); Junichi Ishida, Kyoto (JP); Yoko Moroki, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 250 days.

(21) Appl. No.: 10/903,818

(22) Filed: Jul. 30, 2004

(65) Prior Publication Data

US 2005/0027203 A1 Feb. 3, 2005

(30) Foreign Application Priority Data

Jul. 30, 2003 (JP) ............................. 2003-203690

(51) Int. Cl.
*A61B 5/0408* (2006.01)
(52) U.S. Cl. ...................... 600/393; 600/509
(58) Field of Classification Search ................ 600/393, 600/509
See application file for complete search history.

(56) References Cited

U.S. PATENT DOCUMENTS

| | | | |
|---|---|---|---|
| 4,444,200 A | | 4/1984 | Fujisaki et al. |
| 4,535,783 A | * | 8/1985 | Marangoni .................. 600/524 |
| 4,596,256 A | | 6/1986 | Coustenoble et al. |
| 4,844,090 A | * | 7/1989 | Sekine ....................... 600/509 |
| 5,172,698 A | | 12/1992 | Stanko |
| 5,339,823 A | * | 8/1994 | Reinhold, Jr. ............... 600/523 |
| D475,462 S | * | 6/2003 | Maeda et al. .............. D24/167 |
| 2003/0097078 A1 | * | 5/2003 | Maeda ....................... 600/509 |
| 2003/0187363 A1 | * | 10/2003 | Alroy ......................... 600/509 |
| 2004/0260190 A1 | * | 12/2004 | Tanabe et al. .............. 600/509 |

FOREIGN PATENT DOCUMENTS

| | | |
|---|---|---|
| DE | 26 03 628 A1 | 8/1977 |
| JP | 61-041438 | 2/1986 |
| JP | 03-091304 | 4/1991 |
| JP | 03-091305 | 4/1991 |
| JP | 4-89030 * | 3/1992 |
| JP | 2002-125948 * | 5/2002 |
| JP | 2003-144403 | 5/2003 |

OTHER PUBLICATIONS

European Search Report dated Jan. 30, 2006.
European Search Report dated Apr. 18, 2005.

* cited by examiner

*Primary Examiner*—Lee S. Cohen
(74) *Attorney, Agent, or Firm*—Baker & Daniels LLP

(57) ABSTRACT

A portable electrocardiograph and method of use are disclosed. According to one aspect of the present invention, a portable electrocardiograph is provided which includes: a rectangular housing having at least a first outer surface and a second outer surface; a first electrode provided on the first outer surface of the housing; an electrode formation face provided on the second outer surface of the housing; and a second electrode provided within the electrode formation face; wherein the electrode formation face includes an electrode region in which the second electrode is positioned and a non-electrode region which is positioned so as to surround the electrode region.

11 Claims, 17 Drawing Sheets

PORTABLE ELECTROCARDIOGRAPH

BACKGROUND OF THE INVENTION

1. Field of the Invention

The present invention relates to a portable electrocardiograph capable of easily measuring and storing electrocardiographic waveforms.

2. Description of the Background Art

Generally, for diagnosing ischemic cardiomyopathies such as angina pectoris and myocardial infarction, an electrocardiograph of the patient is used. Known electrocardiographs for measuring electrocardiographic waveforms include stationary electrocardiographs and portable electrocardiographs.

Stationary electrocardiographs are generally found in medical institutions such as hospitals, and they measure waveforms by attaching electrodes to the body of a patient who lies on a bed or the like. The use of a stationary electrocardiograph is advantageous because it is able to measure various electrocardiographic waveforms (such as P waveform and QRS waveform) very precisely. However, stationary electrocardiographs suffer from the fact that, in many cases, the events they are seeking to monitor have past and therefore a proper diagnosis is not possible.

Portable electrocardiographs generally include Holter electrocardiographs and event-type electrocardiographs. Holter electrocardiographs are used to continuously measure and store electrocardiographic waveforms using electrodes which are attached to the body of a patient on a continual basis over a period of days. Event-type electrocardiographs operate by having electrodes applied to the body when a subjective symptom to be measured such as palpitation or pain occurs.

Holter electrocardiographs are very reliable for measuring abnormal waveforms. However, since this method requires that the electrodes remain attached for a period of days, patients are greatly inconvenienced and subject to a great deal of pain and discomfort.

The event-type electrocardiographs generally fall into one of two categories. A first category is comprised of devices which use electrodes which are always in contact with a predetermined region of the body. A second category is comprised of devices which are applied to the body when a subjective symptom to be measured occurs, and the test subject himself/herself makes an electrode comes in contact with the body.

In the first category of event-type portable electrocardiographs, like the Holter portable electrocardiograph, a state where the electrode is always in contact with the body has to be maintained, so that the test subject is inconvenienced. In contrast, in the second category of event-type portable electrocardiographs, it is sufficient to attach the electrode to the body when necessary, so that the portable cardiograph is very easy-to-use for the test subject.

Within the second category of event-type portable electrocardiographs, devices using various configurations of electrodes and body surfaces have been proposed.

For example, Japanese Patent Laying-Open No. 61-41438 discloses, as shown in FIG. 20, a portable electrocardiograph 100D having a configuration in that a display 150 is provided on a front face 102 side of a housing 101 of an electrocardiograph monitor and three electrodes 110, 120 and 130 to be attached to the body of a test subject are provided on a rear face 103 side. Measurement is carried out by making the three electrodes 110, 120 and 130 come into contact with the chest of the test subject.

Japanese Utility Model Laying-Open No. 3-91304 discloses a portable electrocardiograph 100E having a configuration in that, as shown in FIGS. 21A and 21B, the electrode 110 is attached to the front face 102 of the housing 101, a supporting member 191 extending from the top of the housing 101 along the rear face 103 side of the housing 101 is attached to a top face 104 of the housing 101 by using a hinge 192, and the electrode 120 is provided on the surface of the supporting member 191. At the time of measurement, the supporting member 191 is swung (see FIG. 21C), an electrode formation face of the supporting member 191 and the front face 102 of the housing 101 are arranged to be almost in the same plane, and electrocardiographic waveforms are measured in a state where the two electrodes 110 and 120 are in contact with the chest of the test subject.

Japanese Utility Model Laying-Open No. 3-91305 discloses a portable electrocardiograph 100F having a configuration in that, as shown in FIGS. 22A and 22B, the electrode 110 made of electroconductive rubber is provided on the front face 102 of the housing 101 and the electrodes 120 and 130 are provided on a right side face 106 and a left side face 107, respectively, of the housing 101. At the time of measurement, the test subject holds the housing 101 from the rear face 103 side of the housing so as to make contact with the electrodes 120 and 130 provided on both of the side faces 106 and 107 and makes the electrode 110 provided on the front face 102 come into contact with the chest of the test subject to measure electrocardiographic waveforms.

Japanese Patent Laying-Open No. 2003-144403 discloses a portable electrocardiograph 100G having a configuration in that, as shown in FIG. 23, a negative electrode 110 and a neutral electrode 130 are provided on the top face 104 and a bottom face 105, respectively, which are opposite surfaces of the housing 101 having an almost rectangular parallelepiped shape, and a positive electrode 120 is provided on the left side face 107 which is a curved surface adjacent to the faces on which the negative electrode 110 and the neutral electrode 130 are provided. On the front face 102 of the housing 101, the display 150 for displaying a measurement result and an operation button part 140 in which various operation buttons typified by a power source button 141 for turning on the power source are provided.

At the time of measurement, the test subject himself/herself holds the negative electrode 110 and the neutral electrode 130 provided on the top face 104 and the bottom face 105, respectively, from the rear side of the housing 101 by his/her right hand and makes the electrode provided on the left side face 107 of the housing 101 come into contact with his/her chest to measure electrocardiographic waveforms.

In such a portable electrocardiograph having an electrode on the outer surface of the housing, the contact portion between the electrode and the body has to be kept stable throughout the entire measurement period, which may be tens seconds. In the case where stable contact is not maintained, the measured electrocardiographic waveforms are disturbed and cannot be measured with precision.

In the conventional portable electrocardiographs, the contact between the electrode and the measured body is generally maintained by manually pressing the electrocardiograph main body against the measured body at the time of measurement. More specifically, the wrist of the holding hand, forearm, elbow or the like is pressed against the body of the user, thereby preventing the holding hand from being moved during measurement and stably maintaining the contact between the electrode and the body. This point will be described more specifically with reference to portable electrocardiograph 100G disclosed in Japanese Patent Laying-Open No. 2003-144403.

FIG. 24 is a diagram showing a measurement posture to be taken by the test subject at the time of measuring electrocardiographic waveforms by using the portable electrocardiograph 100G disclosed in Japanese Patent Laying-Open No. 2003-144403. As shown in FIG. 24, upon measurement, a test subject 200 presses the wrist portion of a forearm 220 against a portion of the right side of the body while holding the portable electrocardiograph 100G with his/her right hand 210 while also contacting the positive electrode 120 provided on the left side face 107 of the housing 101 of the portable electrocardiograph 100G with the skin of a left lower part of a chest 250. While maintaining contact for tens of seconds, electrocardiographic waveforms are measured.

FIG. 25 shows a state where the portable electrocardiograph 100G is held by the right hand 210. As shown in FIG. 25, the test subject 200 holds the housing 101 while covering the rear face side of the housing 101 with the palm so that the front face 102 of the portable electrocardiograph 100G faces upward. The housing 101 is held by lightly bending a forefinger 212, a middle finger 213, a ring finger 214 and a little finger 215 of the right hand 210 so that any or all of them come into contact with the negative electrode 110 provided for the top face 104 of the housing 101. A thumb 211 extends along the bottom base 105 of the housing 101 to hold the housing 101 while being in contact with the neutral electrode 130 provided on the bottom face 105. The wrist portion of the right hand 210 is pressed against the right side of the body and the right hand 210 is fixed so that the positive electrode 120 formed on the left side face 107 of the housing 101 is not apart from the body.

In the case of measuring the electrocardiographic waveforms in such a measurement posture, if the wrist of the right hand is covered with cloth, the right hand and the right side of the body are not in direct contact with each other. Consequently, a measurement circuit in this portion (an electric circuit formed in the body from the positive electrode to the negative electrode) can be prevented from being short-circuited, so that electrocardiographic waveforms can be measured with high precision. In the case where the test subject does not wear cloth or wears cloth such as a short-sleeve shirt with which the wrist is not covered, the right hand and the right side of the body come into direct contact with each other. In this portion, the measurement circuit is short-circuited. Consequently, the measurement circuit does not cross the heart, so that electrocardiographic waveforms cannot be measured with precision. In such a state, it is difficult to detect ischemic cardiomyopathies of an early stage and the object itself of measuring electrocardiographic waveforms may be lost.

However, if the wrist is not fixed by pressing the right hand against the right side of the body, the contact between the electrode and the body becomes unstable and a large disturbance occurs in the measured electrocardiographic waveforms. In many cases, the test subject uses a portable electrocardiograph when he/she feels palpitation, pant, dizzy or the like. In such a state, it is very difficult to stably maintain the contact between the electrode and the body and the body moves inevitably at the time of measurement.

SUMMARY OF THE INVENTION

An object of the present invention is to provide a portable electrocardiograph which consistently enables stable contact between an electrode and the human body.

A portable electrocardiograph according to a first aspect of the present invention allows a user to measure electrocardiographic waveforms by holding a first electrode provided on an outer surface of a housing element, while pressing a second electrode provided on an outer surface of the housing element against the user's body. An electrode formation face as a face on which the second electrode is provided on the outer surface of the housing includes, in plan view, an electrode region at which the second electrode is positioned and a non-electrode region which is positioned so as to surround the electrode region. The non-electrode region is formed to be flat.

In the portable electrocardiograph according to the first aspect of the present invention, preferably, the electrode region is positioned at a center portion of the electrode formation face.

In the portable electrocardiograph according to the first aspect of the present invention, preferably, a main face of the electrode region is formed to be flat.

In the portable electrocardiograph according to the first aspect of the present invention, preferably, the main face of the electrode region is flush with a main face of the non-electrode region.

In the portable electrocardiograph according to the first aspect of the present invention, preferably, the main face of the electrode region may be positioned so as to be projected from the main face of the non-electrode region.

In the portable electrocardiograph according to the first aspect of the present invention, preferably, a plurality of projections are provided in the non-electrode region.

In the portable electrocardiograph according to the first aspect of the present invention, preferably, when the main face of the electrode region is positioned so as to be projected from that of the non-electrode region and a plurality of projections are provided in the non-electrode region, the electrode formation face is constructed so that a distance between the apex of each of the plurality of projections and the main face of the non-electrode region is equal to or shorter than a distance between the main face of the projected electrode region and the main face of the non-electrode region.

In the portable electrocardiograph according to the first aspect of the present invention, preferably, a plurality of recesses are provided in the non-electrode region.

In the portable electrocardiograph according to the first aspect of the present invention, preferably, the housing has an almost rectangular parallelepiped shape, the first electrode is provided in a grip region including a first end face positioned at an end in the longitudinal direction of the housing, and the second electrode is provided on a second end face positioned at the other end in the longitudinal direction of the housing.

In the portable electrocardiograph according to the first aspect of the present invention, preferably, the housing has an almost rectangular parallelepiped shape, the first electrode is provided in a grip region positioned adjacent to a first end face positioned at an end in the longitudinal direction of the housing, and the second electrode is provided on a second end face positioned at the other end in the longitudinal direction of the housing.

A portable electrocardiograph according to a second aspect of the present invention includes: a housing having an almost rectangular parallelepiped shape; a first electrode provided in a grip region positioned adjacent to an end in the longitudinal direction of the housing; and a second electrode provided on a second end face positioned at the other end in the longitudinal direction of the housing. The user measures electrocardiographic waves by holding the grip region by his/her right hand and, simultaneously, pressing the second end face against the limbs other than the holding hand or the trunk. The second end face includes an electrode region on which the second electrode is positioned and a non-electrode region which is positioned so as to surround the electrode region. The non-electrode region is formed to be flat.

According to the present invention, it is possible to provide a portable electrocardiograph which enables stable contact between an electrode and the human body.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
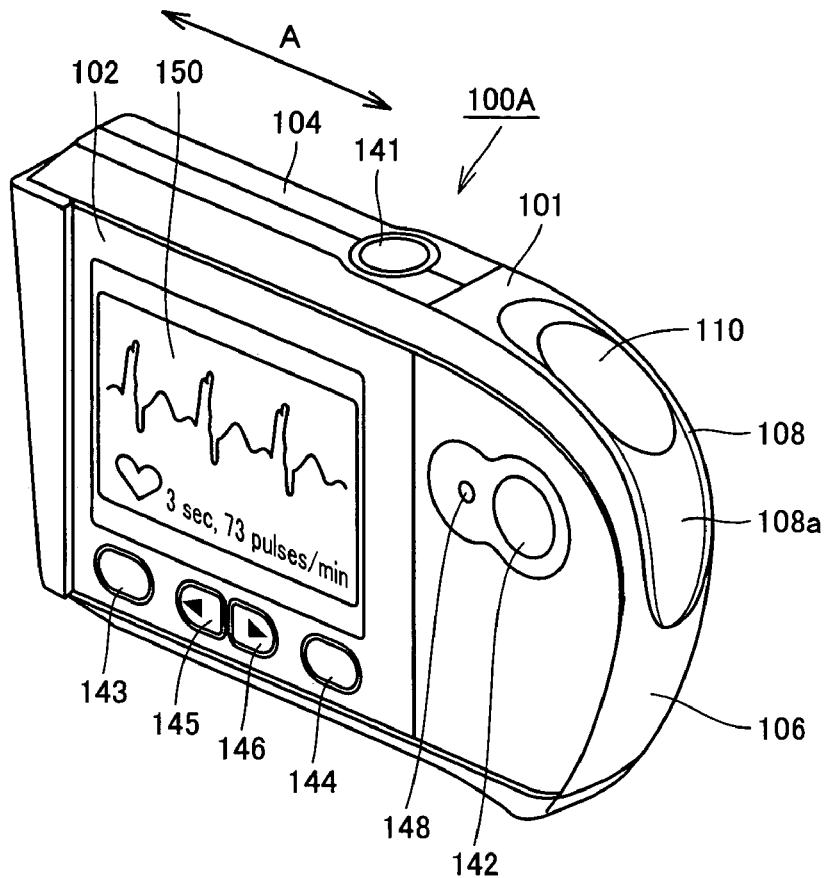
FIG. 1 is a perspective view showing the outside structure of a portable electrocardiograph in a first embodiment of the present invention.

Hereinafter, embodiments of the present invention will be described with reference to the drawings.

First Embodiment

First, the structure of a portable electrocardiograph 100A in the first embodiment will be described. As shown in FIGS. 1 to 6, the portable electrocardiograph 100A in this embodiment is formed light and small so as to be easily handled and can be held by one hand. The portable electrocardiograph 100A has a housing 101 of a flat and elongated almost rectangular parallelepiped shape. On the outer surfaces (front face 102, rear face 103, top face 104, bottom face 105, right side face 106, left side face 107 and curved face 108), a display unit, an operation unit, electrodes and the like are arranged.

Figure 2:
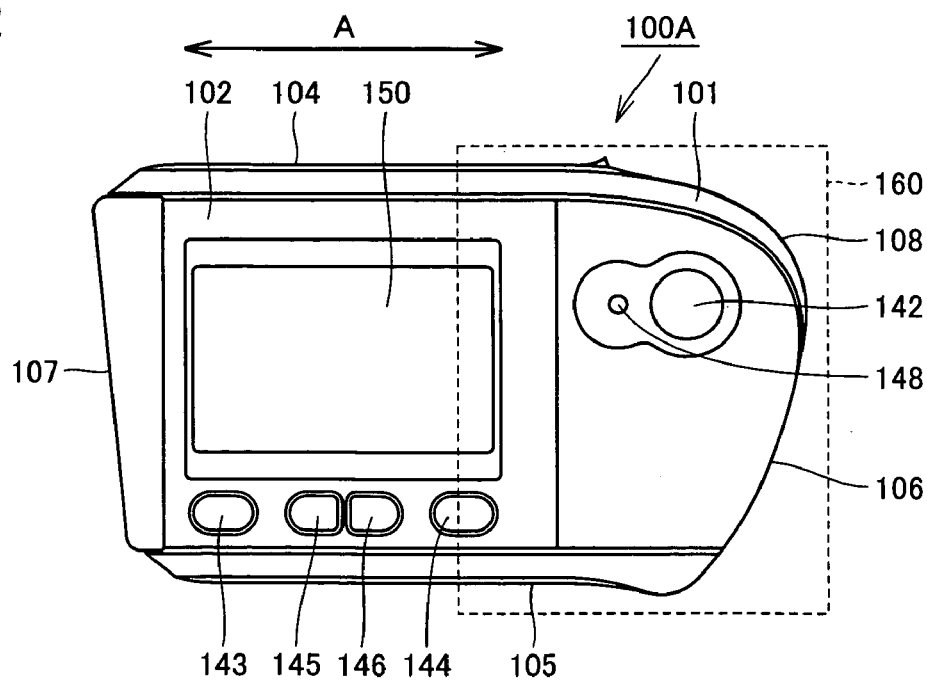
FIG. 2 is a front view of the portable electrocardiograph in the first embodiment of the present invention.

As shown in FIGS. 1 and 2, a grip part 160 as a grip region is provided adjacent to an end in the longitudinal direction (the direction of the arrow A in the figure) of the housing 101. The grip part 160 is a portion provided so that the test subject can stably hold the main body of the portable electrocardiograph 100A at the time of measurement. At the time of measurement, the grip part 160 is covered with the right hand of the test subject. The grip part 160 includes a right side face 106 as a first end face positioned at one end in the longitudinal direction of the housing 101, portions adjacent to one end of each of the front face 102, the rear face 103, the top face 104 and the bottom face 105, and a curved face 108 continued to the right side face 106 and the top face 104.

For the grip part 160 on the front face 102 side of the housing 101, a measurement button 142 as an operation button for starting measurement is provided. A rest 148 on which the thumb of the right hand is rested at the time of measurement is provided on the front face 102 of the housing 101 so as to be adjacent to the measurement button 142.

At the front face 102 adjacent to the other end in the longitudinal direction of the housing 101, a display 150 is positioned. The display 150 is constructed by, for example, a liquid crystal display and is a portion for displaying a result of measurement. The measurement result is displayed as, for example, electrocardiographic waveforms or numerical data as shown in FIG. 1.

Below the display 150 in the front face 102, various operation buttons are disposed. In the illustrated portable electrocardiograph 100A, in the front face 102 of the housing 101, a setting button 143, a display button 144, a left scroll button 145 and a right scroll button 146 are disposed.

The setting button 143 is an operation button for making various settings of the portable electrocardiograph 100A. The display button 144 is an operation button used for displaying a measurement result on the display 150. The left scroll button 145 and the right scroll button 146 are operation buttons for scrolling and displaying a graph of a measurement result, guide information and the like to be displayed on the display 150.

Figure 3:
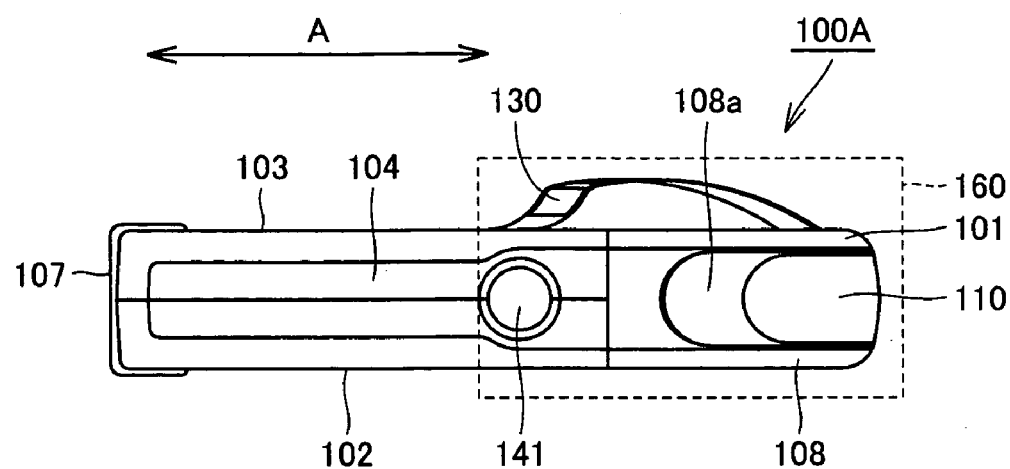
FIG. 3 is a top view of the portable electrocardiograph in the first embodiment of the present invention.

As shown in FIGS. 1 and 3, the power source button 141 is disposed in a predetermined position in the top face 104 of the housing 101. The power source button 141 is an operation button for operating ON/OFF of the portable electrocardiograph 100A.

Figure 4:
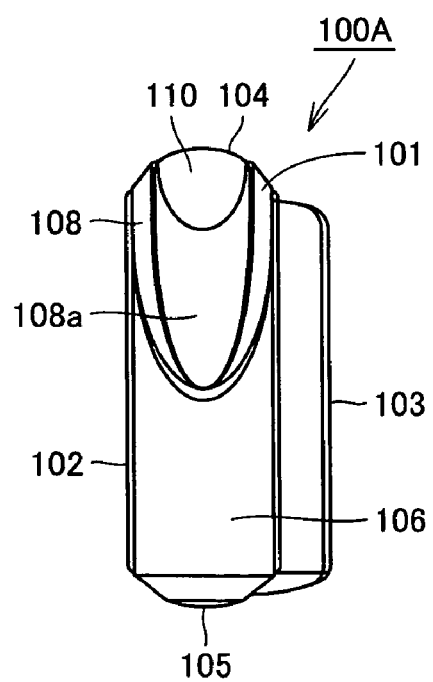
FIG. 4 is a right side view of the portable electrocardiograph in the first embodiment of the present invention.

As shown in FIGS. 1, 3 and 4, a recess 108a is provided in the curved face 108 of the housing 101. The recess 108a extends along the extension direction of the curved face 108. In a predetermined position in the recess 108a, the negative electrode 110 as a first electrode is provided. The negative electrode 110 is made of an electroconductive material and has a shape which is slightly projected to the outside from the curved face of the recess 108a and is exposed in the recess 108a. The recess 108a is formed in a shape for accepting the forefinger of the right hand.

Figure 5:
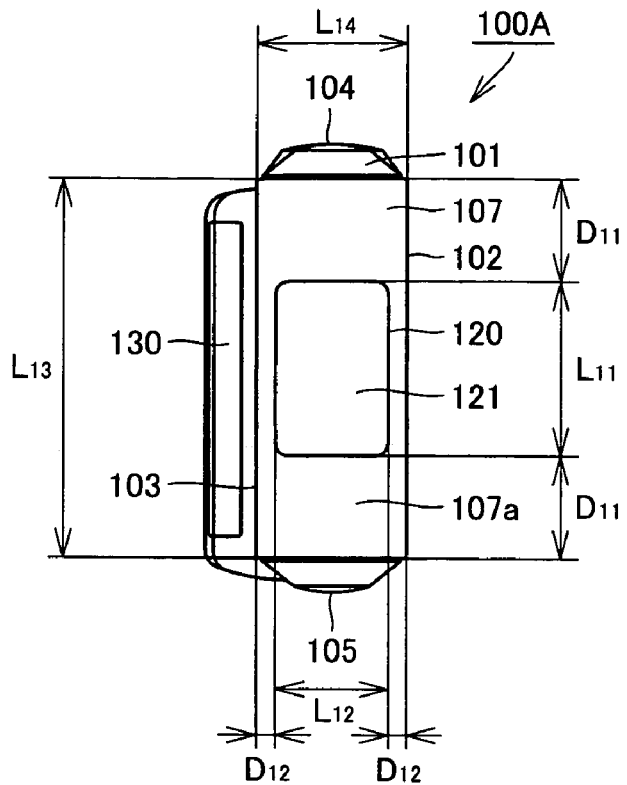
FIG. 5 is a left side view of the portable electrocardiograph in the first embodiment of the present invention.

As shown in FIGS. 1 and 5, the positive electrode 120 as a second electrode is provided for the left side face 107 as a second end face positioned at the other end in the longitudinal direction of the housing 101. The positive electrode 120 is made of an electroconductive material and is positioned at a center position in the left side face 107 of the housing 101. A contact face 121 with the body, which is the main face of the positive electrode 120 is formed to be flat. Around the positive electrode 120, a flat face 107a made of an insulating material is formed. The flat face 107a is flush with the contact face 121 of the positive electrode 120.

Specifically, the left side face 107 of the housing 101 as an electrode formation face is constructed by an electrode region at which the positive electrode 120 is positioned (i.e., the contact face 121 of the positive electrode 120) and a non-electrode region (i.e., the flat face 107a) positioned so as to surround the electrode region and formed to be flat. The main face of the electrode region and that of the non-electrode region are flush with each other.

The contact face 121 of the positive electrode 120 has an almost rectangle shape and, preferably, the length of one side of the contact face 121 lies in the range from 20 mm to 30 mm. The width of the non-electrode region extending from the border with the electrode region to the end of the electrode formation face is, preferably, at least 2 mm. In the portable electrocardiograph 100A in this embodiment, the size of the electrode region ($L_{11} \times L_{12}$ FIG. 5) is 30 mm×20 mm and the size of the electrode formation face ($L_{13} \times L_{14}$ in FIG. 5) is 62 mm×27 mm. The width of the non-electrode region from the border with the electrode region to the end of the electrode formation face ($D_{11}$ and $D_{12}$ in FIG. 5) is 16 mm in the longitudinal direction of the electrode formation face and is 3.5 mm in the transverse direction.

Figure 6:
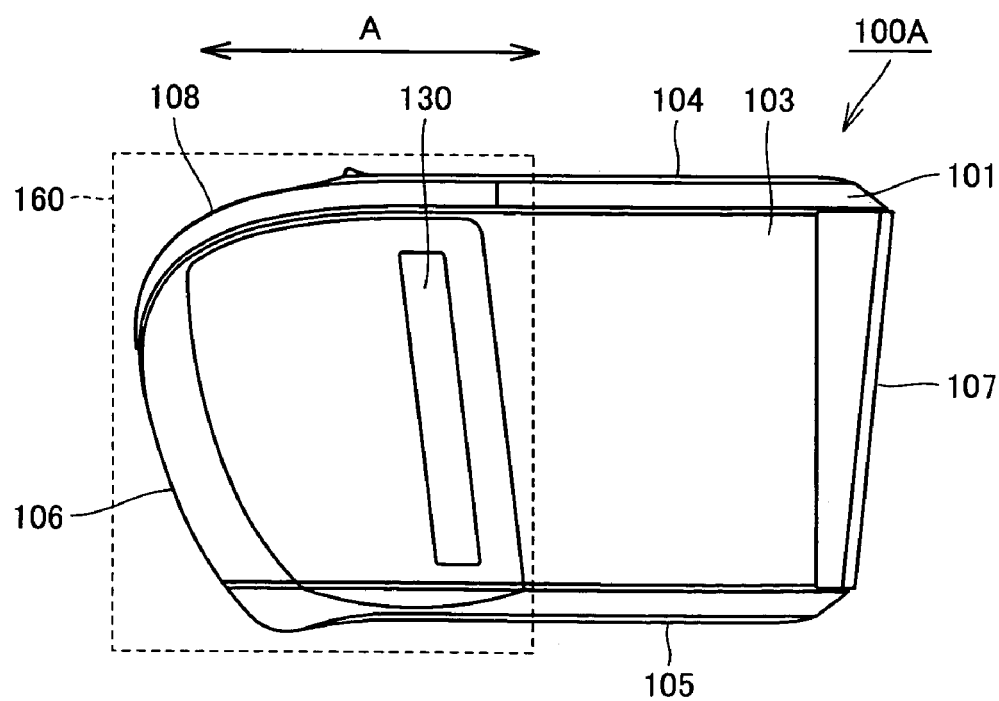
FIG. 6 is a rear view of the portable electrocardiograph in the first embodiment of the present invention.

As shown in FIG. 6, in the grip part 160 on the rear face 103 side of the housing 101, the neutral electrode 130 as an indifferent electrode is positioned. The neutral electrode 130 is made of an electroconductive material and extends in the vertical direction on the rear face 103 of the housing 101. The neutral electrode 130 extends in the direction crossing the longitudinal direction on the rear face 103 of the housing 101 and is inclined so that its upper end portion (an end portion on the top face 104 side) is positioned to the right side face 106 side more than its lower end portion (an end portion on the bottom face 105 side). The neutral electrode 130 is an electrode for detecting potential fluctuations occurring in the human body at the time of measurement and for obtaining a correction value for removing an error component included in a measurement result.

Next, a measurement posture to be taken by the test subject in the case of using the portable electrocardiograph 100A having the above configuration will be described.

Figure 7:
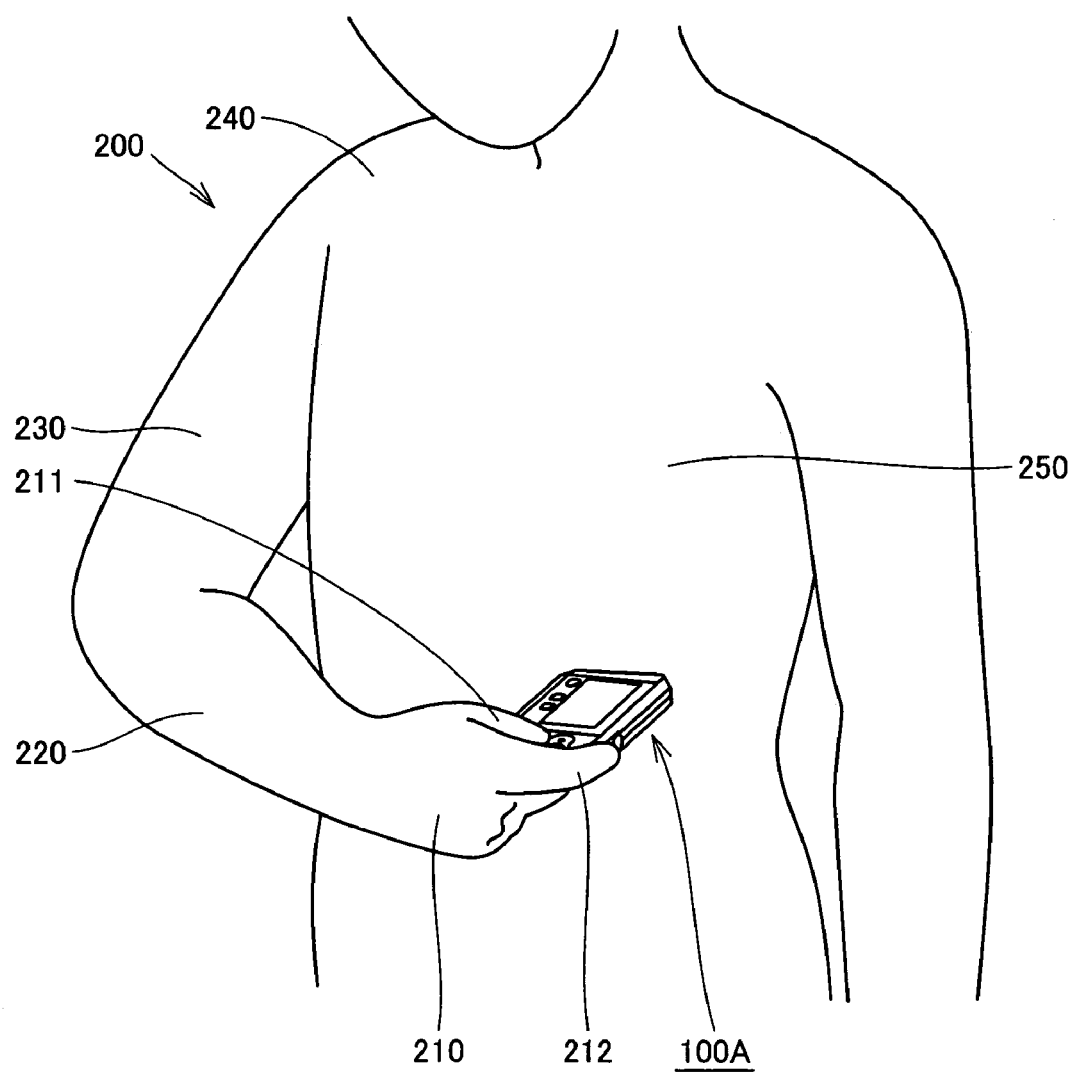
FIG. 7 is a diagram showing a measurement posture to be taken by the test subject at the time of measuring electrocardiographic waveforms by using the portable electrocardiograph in the first embodiment of the present invention.

As shown in FIG. 7, at the time of measurement, the test subject 200 makes the positive electrode 120 provided on the left side face 107 of the housing 101 come into direct contact with the skin on the fifth intercostal anterior axillary line positioned at a lower left portion of the chest 250 while holding the grip part 160 of the portable electrocardiograph 100A by the right hand 210. The measurement button 142 provided on the front face 102 of the housing 101 is depressed by the thumb 211 of the right hand 210, and the thumb 211 of the right hand 210 is rested on the rest 148. While maintaining the state for tens of seconds, electrocardiographic waveforms are measured.

The gripping state of the portable electrocardiograph 100A by the right hand 210 will now be described.

Figure 8A:
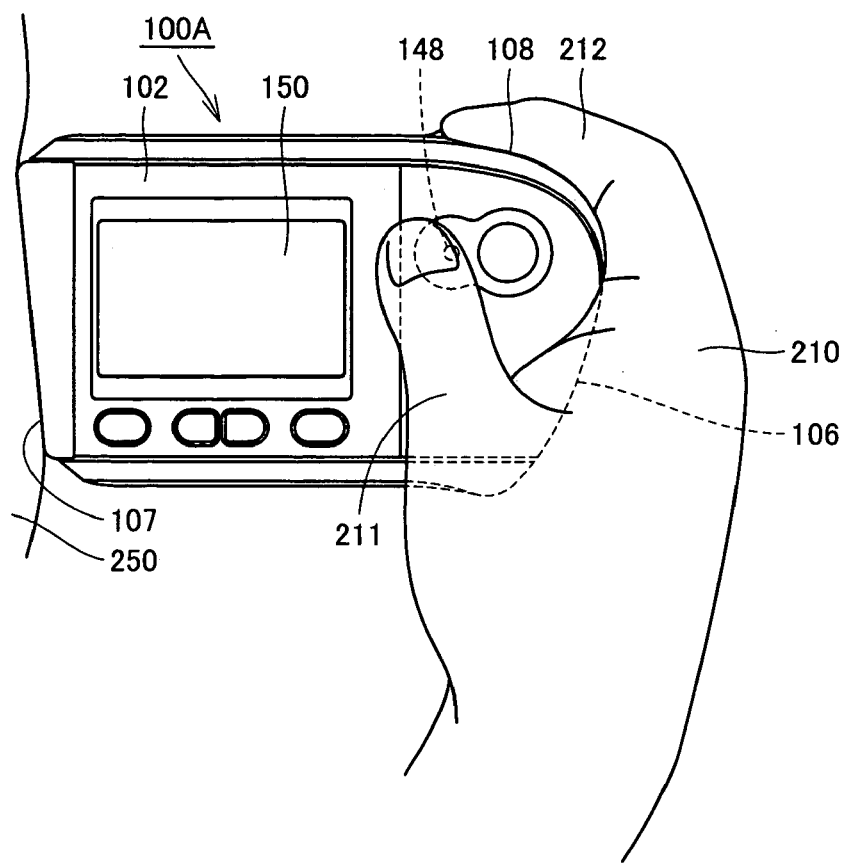
FIG. 8A is a front view of the portable electrocardiograph in the first embodiment of the present invention, showing a state where the portable electrocardiograph is held by the right hand at the time of measuring electrocardiographic waveforms.
Figure 8B:
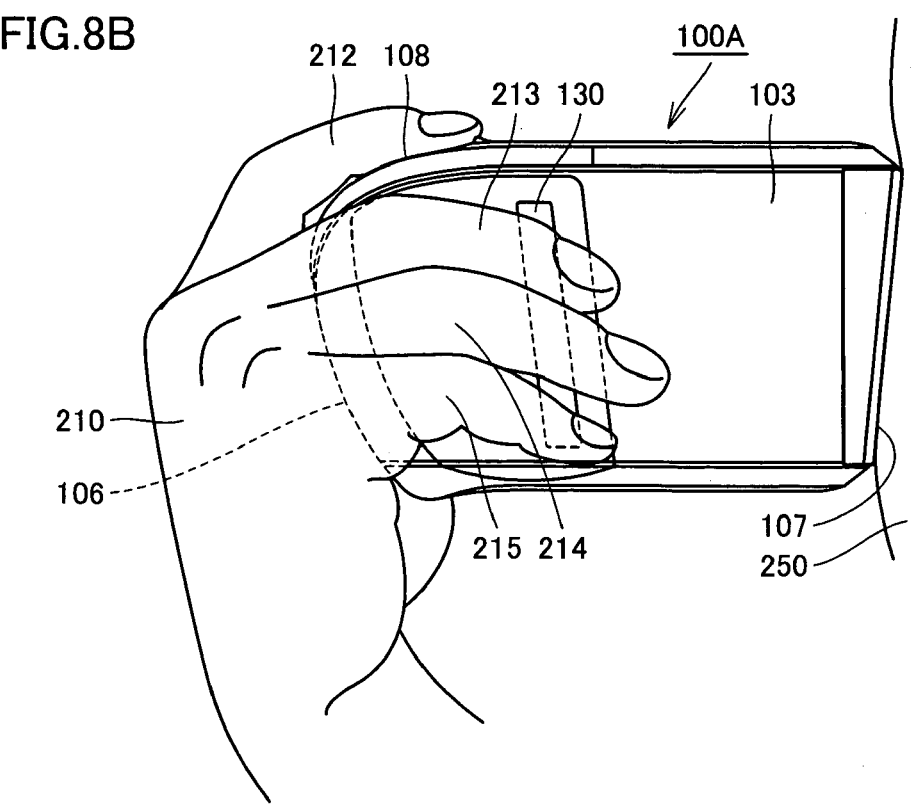
FIG. 8B is a rear view of the portable electrocardiograph in the first embodiment of the present invention, showing a state where the portable electrocardiograph is held by the right hand at the time of measuring electrocardiographic waveforms.

As shown in FIG. 8A, in the measurement posture, the test subject 200 holds the grip part 160 of the housing 101 by the right hand 210 while covering the right side face 106 of the housing 101 with the palm so that the front face 102 of the portable electrocardiograph 100A faces upward. At this time, the thumb 211 is lightly bent and attached to the housing 101 so that the thumb 211 of the right hand 210 comes into contact with the rest 148 provided adjacent to one end of the front face 102 of the housing 101. The forefinger 212 is lightly bent so as to be along the curved face 108 of the housing 101 and is fit in the recess 108 a provided in the curved face 108 so as to come into contact with the negative electrode 110. Further, as shown in FIG. 8B, the grip part 160 of the rear face 103 of the housing 101 is held by the middle finger 213, the ring finger 214 and the little finger 215 of the right hand 210. At this time, at least one of the middle finger 213, the ring finger 214 and the little finger 215 on the rear face 103 side of the housing 101 comes into contact with the neutral electrode 130 provided on the rear face 103 of the housing 101.

Figure 9:
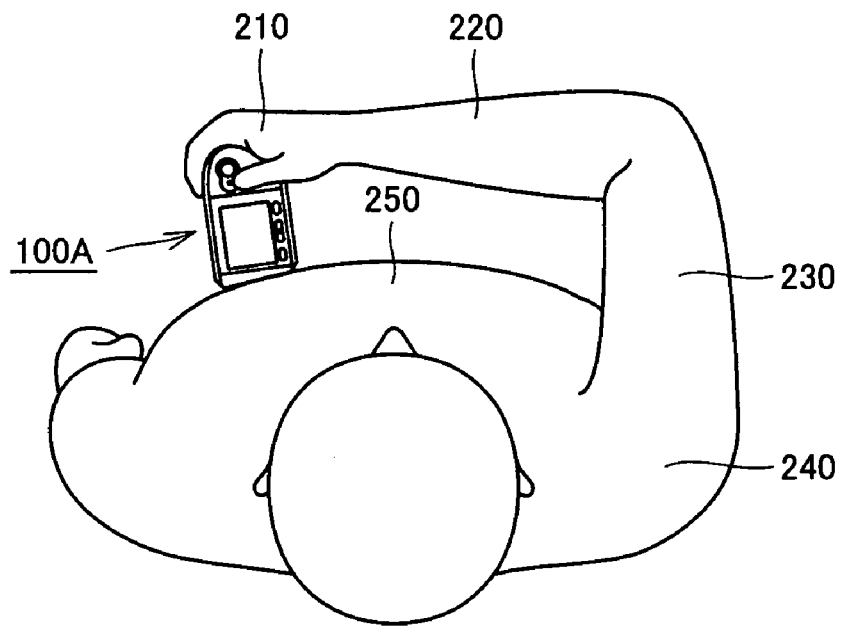
FIG. 9 is a diagram showing from above a measurement posture to be taken in the case where the test subject does not wear cloth at the time of measuring electrocardiographic waveforms by using the portable electrocardiograph in the first embodiment of the present invention.

As shown in FIG. 9, in the portable electrocardiograph 100A in this embodiment, at the time of measurement, the housing 101 is held so that the right side face 106 of the housing 101 may be covered with the palm of the right hand 210. Consequently, the wrist of the right hand 210 is always apart from the chest 250 only by predetermined distance. Accordingly, the right arm (the forearm 220 and the upper arm 230) does not come into contact with the chest 250. As a result, a measurement circuit is constructed extending from the right hand 210 holding the negative electrode 110 and the neutral electrode 130 via the forearm 220 which is not in contact with the chest 250 and the upper arm 230 and a right shoulder 240 which are also not in contact with the chest 250 to the chest 250 against which the positive electrode is pressed. Consequently, the measurement posture by which the measurement circuit is constructed so as to cross the heart can be realized with reliability, and the measurement circuit can be prevented from being short-circuited due to contact between the right hand 210, the forearm 220 and the upper arm 230 and the chest 250.

Figure 10:
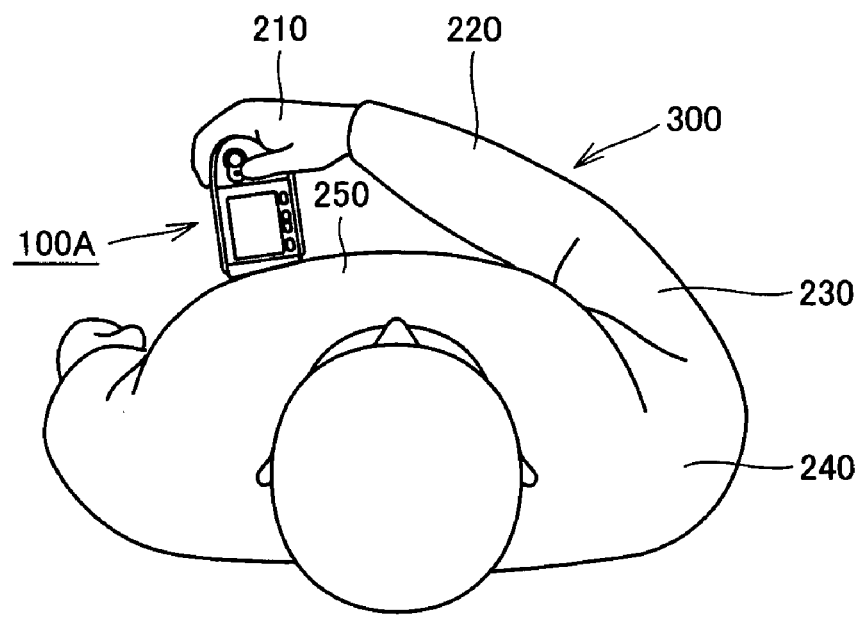
FIG. 10 is a diagram showing from above a measurement posture to be taken in the case where the test subject wears cloth at the time of measuring electrocardiographic waveforms by using the portable electrocardiograph in the first embodiment of the present invention.

As shown in FIG. 10, when the test subject 200 wears cloth 300 covering the right elbow, the right hand 210 can be fixed by making the right elbow come in contact with the right side of the body. By taking the measurement posture that the right elbow is pressed against the right side of the body, the measurement posture shown in FIG. 10 can be maintained for tens of seconds without moving the right hand 210. As a result, the electrocardiographic waveforms can be measured stably with high precision.

As described above, in the portable electrocardiograph 100A in this embodiment, the left side face 107 as the electrode formation face includes the electrode region at which the position electrode 120 is positioned and the non-electrode region formed to be flat so as to surround the electrode region. With such a configuration, the contact stability between the contact face 121 of the positive electrode 120 and the chest 250 is improved, the measurement voltage value is not varied, and electrocardiographic waveforms can be measured stably with high precision. Those are effects attained by providing the non-electrode region in the electrode formation face. This point will be described in detail below.

There are various noise components entering a voltage value obtained at the time of measurement. One of the noise components which exerts an influence on the voltage value most is a change in the contact area between the positive electrode and the chest which occurs due to movement of the test subject. When the contact area between the positive electrode and the chest changes, the contact resistance in the portion largely fluctuates and large variations occur in the voltage value obtained. To suppress variations in the measured voltage value, the test subject has to maintain the measurement posture as shown in FIG. 7 without moving the right hand and the chest at the time of measurement. However, in many cases, the test subject feels palpitation, pant, dizzy or the like at the time of measurement and it is very difficult for the test subject to maintain the measurement posture. Consequently, the body of the test subject moves inevitably at the time of measurement.

In the portable electrocardiograph 100A in this embodiment, however, the non-electrode region formed so as to surround the contact face 121 is positioned around the contact face 121 of the positive electrode 120 as the electrode region. Consequently, fluctuations of the contact region which occur due to movement of the right hand 210 and the chest 250 occur only in the non-electrode region and hardly occur in the electrode region. Therefore, the contact with the chest 250 of the positive electrode 120 positioned at the center portion of the electrode formation face is maintained more stably. Even if the test subject moves, a change does not occur in the contact area between the positive electrode 120 and the chest 250. As a result, a measurement voltage value can be obtained accurately. Thus, the electrocardiographic waveforms can be measured stably with high precision.

As described above, by employing the portable electrocardiograph 100A as in this embodiment, also in the case where the test subject takes the measurement posture as shown in FIG. 9, stable contact between the electrode and the body can be realized without fixedly pressing the hand holding the electrocardiograph main body against another region of the body, and electrocardiographic waveforms can be stably measured with high precision. In the case where the test subject takes the measurement posture as shown in FIG. 10, the right hand is stabilized by pressing the right elbow against the chest, so that electrocardiographic waveforms can be measured more precisely and stably.

In the case of employing the portable electrocardiograph 100A as in this embodiment, electrocardiographic waveforms can be measured by pressing the positive electrode as the second electrode against the palm of the left hand or the inner side of the thigh of the left leg.

A test of verifying how much electrocardiographic waveforms are stabilized by employing the structure of the portable electrocardiograph 100A will be described below.

Figure 12:
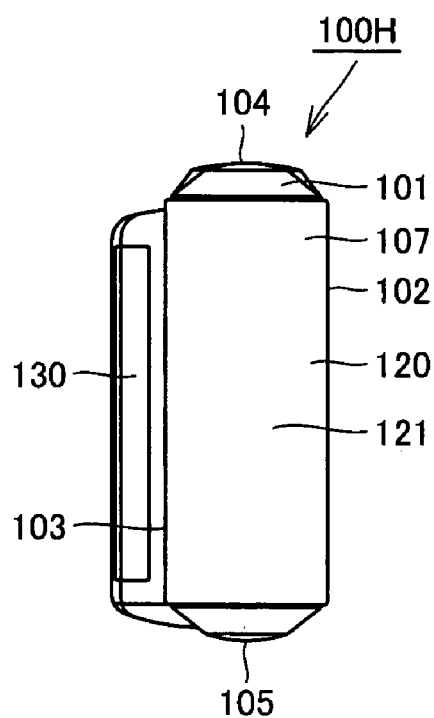
FIG. 12 is a left side view of the portable electrocardiograph used as the comparative example in the verification test of contact stability.

In the test, the portable electrocardiograph 100A was used as an example and a portable electrocardiograph 100H shown in FIG. 12 was used as a comparative example. The portable electrocardiographs were used under the same conditions and stabilities of the measured electrocardiographic waveforms were compared with each other, thereby evaluating the contact stability between the electrode and the body.

Figure 11:
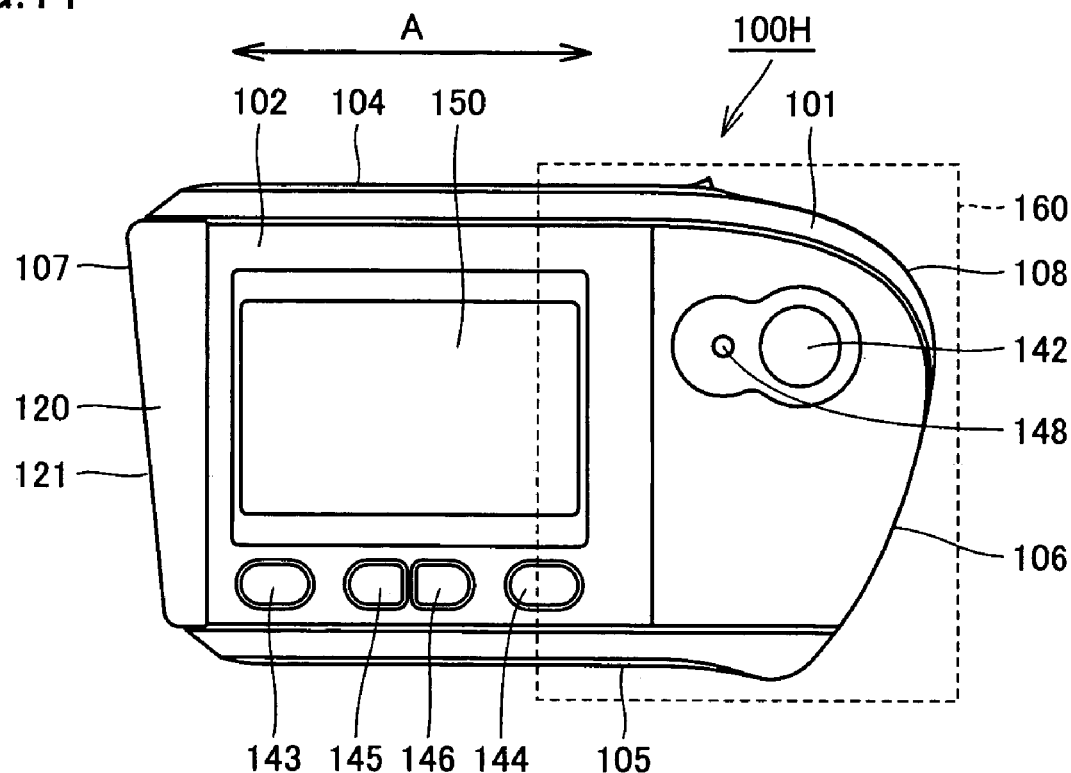
FIG. 11 is a front view of a portable electrocardiograph used as a comparative example in a verification test of contact stability.

First, the structure of the portable electrocardiograph 100H used as a comparative example will be described. As shown in FIGS. 11 and 12, the structure of the portable electrocardiograph 100H is similar to that of the portable electrocardiograph 100A except for the structure of the left side face 107 of the housing 101 as an electrode formation face.

As shown in FIGS. 11 and 12, the positive electrode 120 as the second electrode is provided on the left side face 107 as a second end face positioned at the other end in the longitudinal direction of the housing 101 of the portable electrocardiograph 100H. The positive electrode 120 is made of an electroconductive material and extends from the rear face 103 of the housing 101 via the left side face 107 to the front face 102. That is, the positive electrode 120 is formed so that the entire left side face 107 of the housing 101 serves as the contact face 121 with the body. Consequently, the non-electrode region provided on the left side face 107 of the portable electrocardiograph 100A does not exist in the portable electrocardiograph 100H.

The contact face 121 as a main face of the electrode 120 of the portable electrocardiograph 100H has a rectangular shape and is formed to be flat. The size is 62 mm×27 mm.

The differences between the structure of the portable electrocardiograph 100H as the comparative example and the structure of the portable electrocardiograph 100A as the example of the present invention will be summarized as shown in Table 1.

TABLE 1

|  | Size of electrode region | Presence/absence of non-electrode region | Size of electrode formation face | Shape of contact face |
|---|---|---|---|---|
| Comparative example | 62 mm × 27 mm | Absence | 62 mm × 27 mm | Flat |
| Example of the present invention | 30 mm × 20 mm | Presence | 62 mm × 27 mm | Flat |

Figure 13:
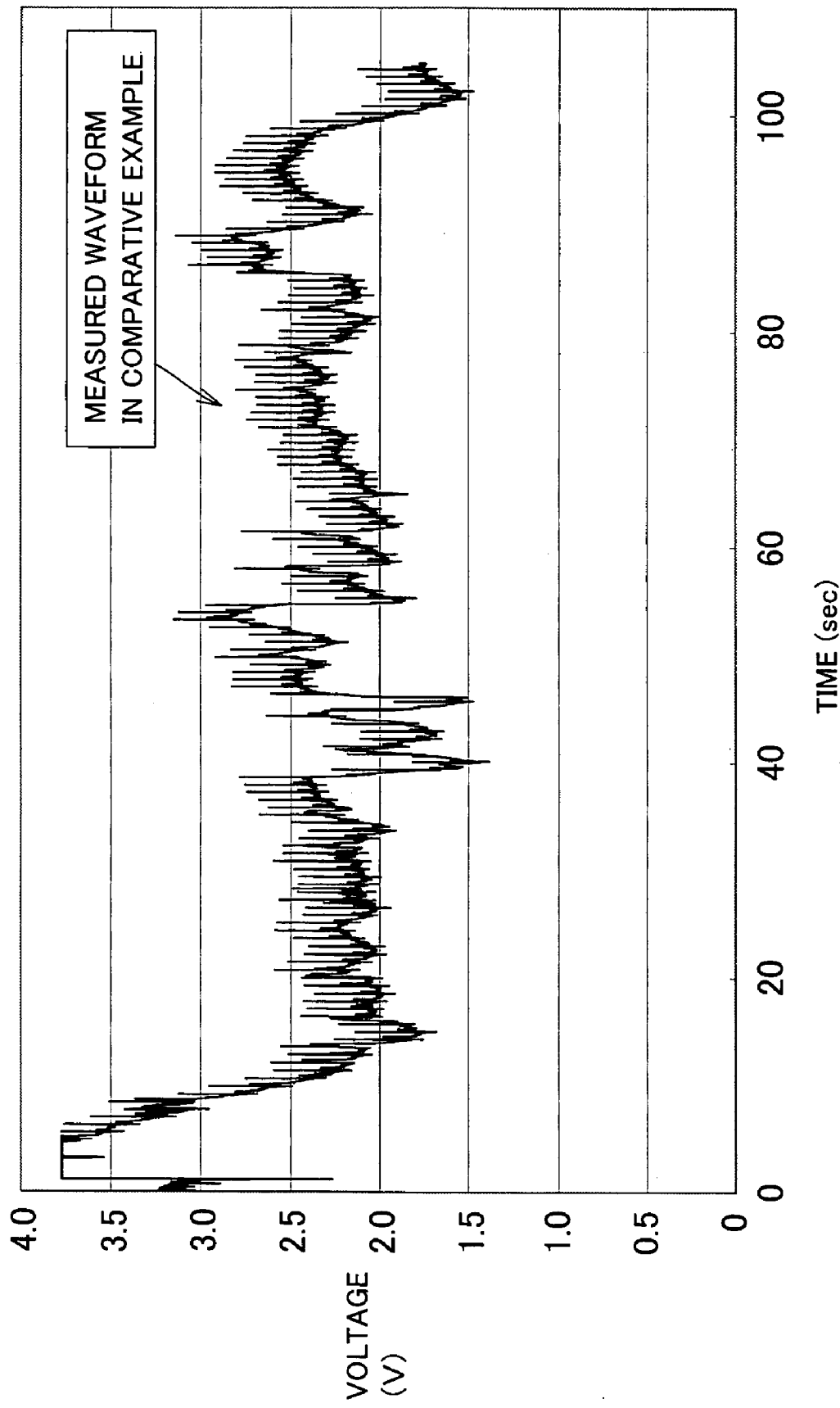
FIG. 13 is a diagram showing electrocardiographic waveforms measured by the portable electrocardiograph in the comparative example in the verification test of contact stability.
Figure 14:
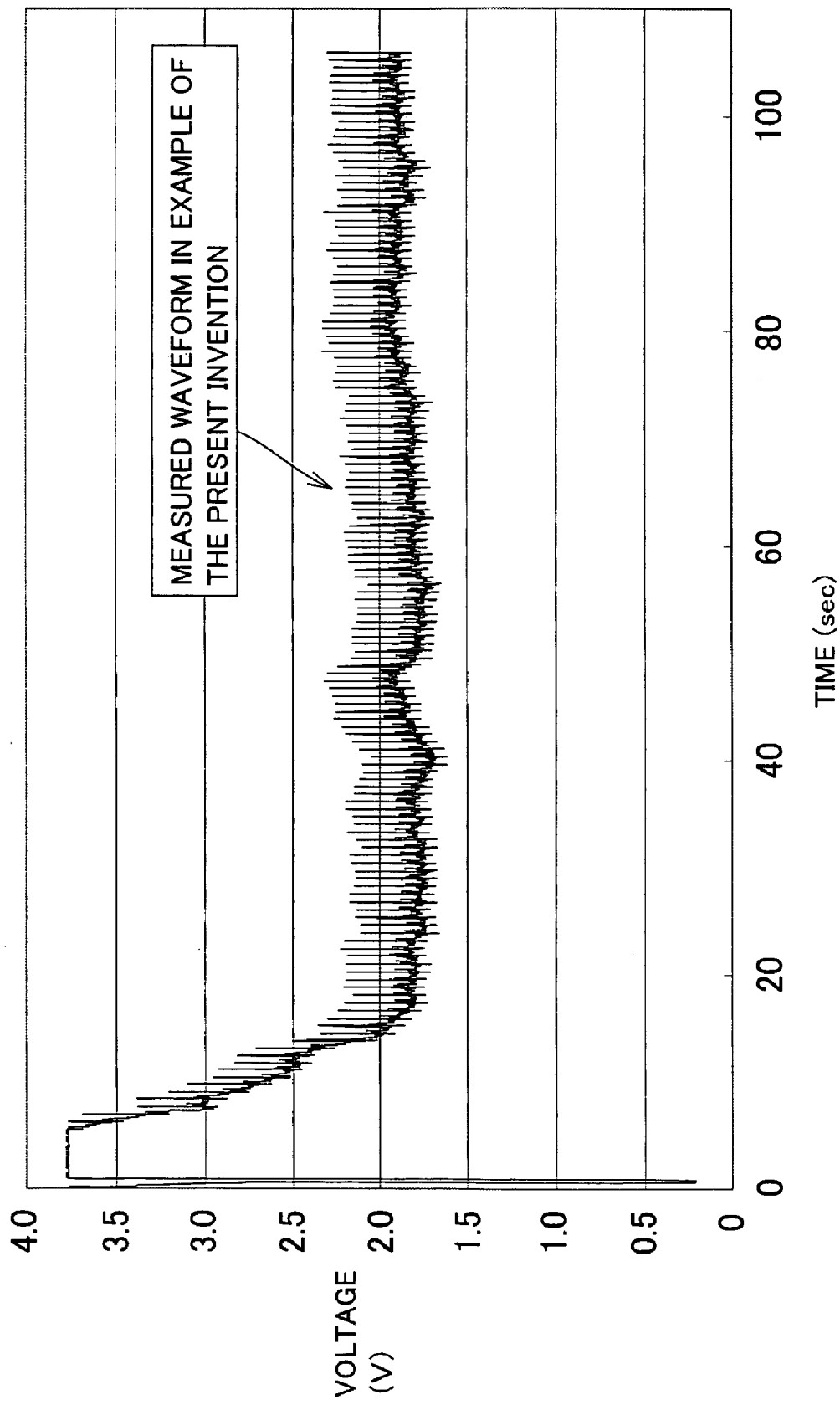
FIG. 14 is a diagram showing electrocardiographic waveforms measured by a portable electrocardiograph in an example of the present invention in a verification test of contact stability.

FIG. 13 is a diagram showing electrocardiographic waveforms obtained by the test subject himself/herself in the measurement posture as shown in FIG. 7 by using the portable electrocardiograph 100H. FIG. 14 is a diagram showing electrocardiographic waveforms measured by the test subject himself/herself in the measurement posture as shown in FIG. 7 by using the portable electrocardiograph 100A. In the diagrams, the horizontal axis denotes time, and the vertical axis denotes a measured voltage value.

In the case of using the portable electrocardiograph 100H in which the entire left side face 107 serves as the contact face 121 of the positive electrode 120 as shown in FIGS. 11 and 12, it is understood that large variations occur in the measured voltage values as shown in FIG. 13. The magnitude of a variation in the measured voltage value is about 1.5 V at the maximum. It is understood that a large fluctuation occurs in the measured voltage value in short time. The fluctuation occurs when the contact area between the positive electrode 120 and the chest changes due to movement of the wrist, chest or the like of the test subject and a large fluctuation occurs in the contact resistance in the portion.

In contrast, it is understood that in the case of using the portable electrocardiograph 100A in which the contact face 121 of the positive electrode 120 is positioned at the center portion of the left side face 107 and the non-electrode region is formed around the contact face 121 as shown in FIGS. 1 to 6, the measured voltage value is very stable as shown in FIG. 14. The magnitude of variations of the measured voltage value is about 0.3 V and is suppressed to about ⅕ of the variation in the portable electrocardiograph 100H. The reason is considered as follows. Also in the case where the wrist, chest or the like of the test subject moves, fluctuations in the contact state between the left side face 107 as the electrode formation face and the chest of the test subject occur only in the non-electrode region and hardly occur in the electrode region, so that the stable contact between the positive electrode 120 and the chest is assured.

Figure 15:
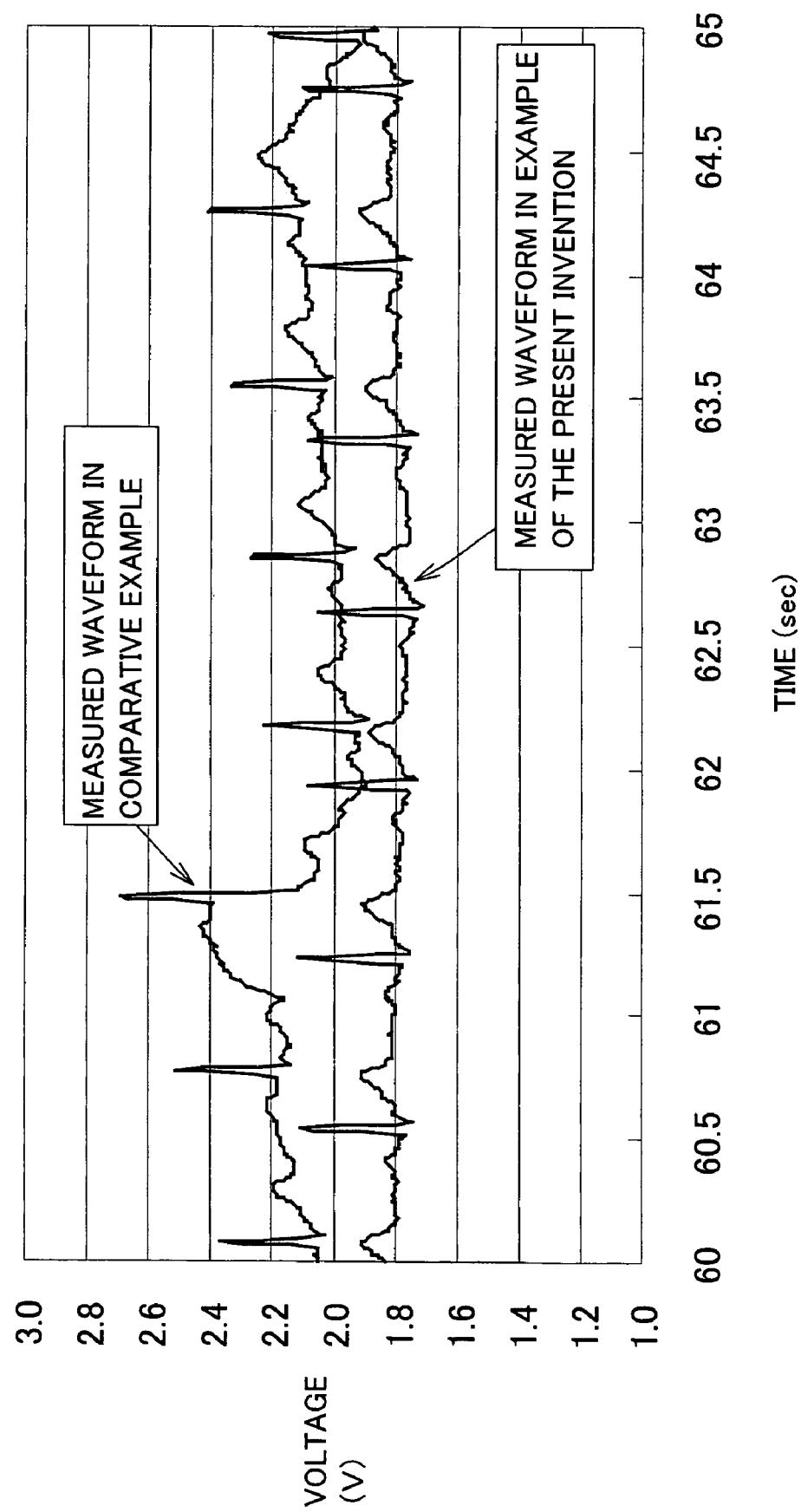
FIG. 15 is a diagram showing comparison between contact stability of the electrocardiographic waveforms in the comparative example and that of the electrocardiographic waveforms in the example of the present invention in the verification test of contact stability.

FIG. 15 is a diagram showing electrocardiographic waves obtained by enlarging the electrocardiographic waves shown in FIGS. 13 and 14 in the time base direction and overlapped for comparison. It is understood from FIG. 15 that, in measured waveforms in the example of the present invention, an electrocardiographic wave obtained by a single stroke has an almost same shape as that of other electrocardiographic waves and is measured stably and precisely. In contrast, in the measured waveforms in the comparative example, a disturbance occurs also in each of the electrocardiographic waves, obtained by a single stroke, and the electrocardiographic waves are not measured stably and precisely. Consequently, it is difficult to determine if the electrocardiographic waves are abnormal or it is a measurement error in the measured waveforms in the comparative example, and measurement itself of abnormal waveforms can be meaningless. On the other hand, in the measured waveforms in the example of the present invention, abnormal electrocardiographic waves and normal ones can be discriminated from each other with reliability and the present invention largely contributes to early finding of ischemic cardiomyopathies.

Second Embodiment

First, the structure of a portable electrocardiograph 100B in a second embodiment will be described. The same reference numerals will be given to components similar to those in the foregoing first embodiment and their description will not be repeated here.

Figure 16:
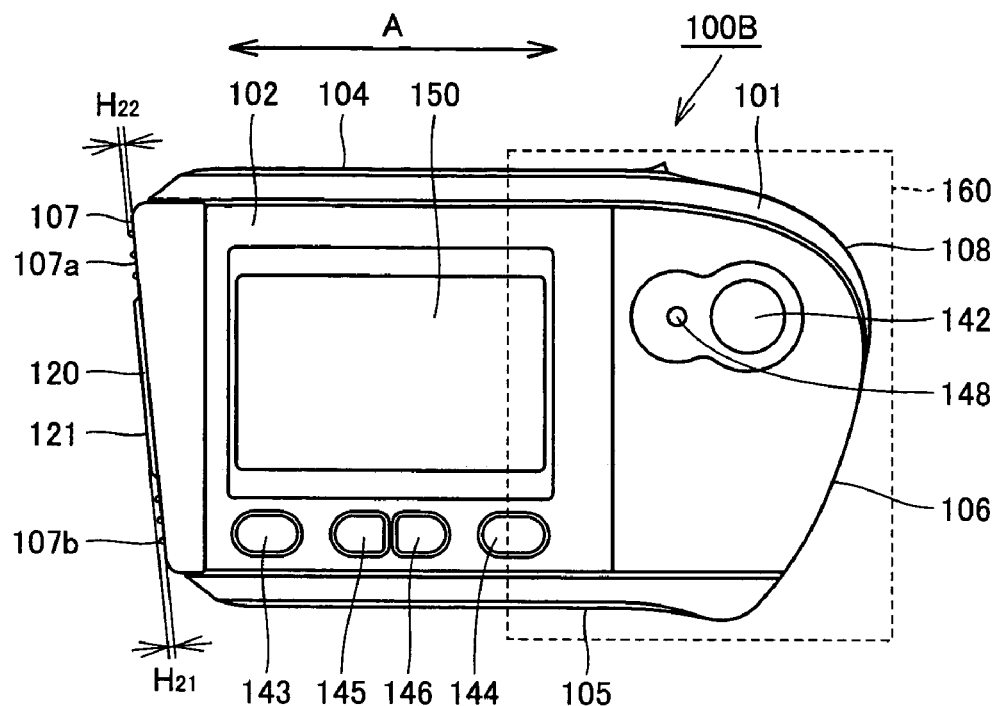
FIG. 16 is a front view of a portable electrocardiograph in a second embodiment of the present invention.
Figure 17:
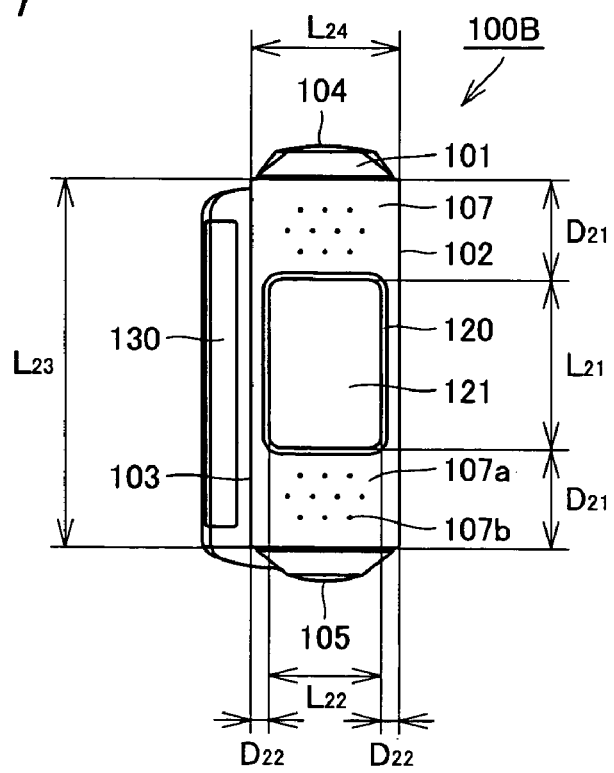
FIG. 17 is a left side view of the portable electrocardiograph in the second embodiment of the present invention.

As shown in FIGS. 16 and 17, the portable electrocardiograph 100B in this embodiment is different from the portable electrocardiograph 100A in the first embodiment only with respect to the structure of the left side face 107 as the electrode formation face of the housing 101.

The portable electrocardiograph 100B in this embodiment has the positive electrode 120 as the second electrode on the left side face 107 of the housing 101. The positive electrode 120 is made of an electroconductive material and is positioned at the center portion of the left side face 107 of the housing 101. Around the positive electrode 120, the flat face 107a made of an insulating material is formed. The contact face 121 with the body as the main face of the positive electrode 120 is provided so as to be projected from the main face of the flat face 107a. The contact face 121 of the positive electrode 120 is formed to be flat.

Specifically, the left side face 107 of the housing 101 as an electrode formation face is constructed by an electrode region in which the positive electrode 120 is positioned (i.e., the contact face 121 of the positive electrode 120) and a non-electrode region (i.e., the flat face 107a) positioned so as to surround the electrode region and formed to be flat. The main face of the electrode region is provided so as to be projected from the main face of the non-electrode region.

The contact face 121 of the positive electrode 120 has an almost rectangle shape and, preferably, the length of one side of the contact face 121 lies in the range from 20 mm to 30 mm. The distance between the main face of the electrode region positioned so as to be projected from the main face of the non-electrode region and the main face of the non-electrode region is preferably 1 mm or less. The width of the non-electrode region extending from the border with the electrode region to the end of the electrode formation face is, preferably, at least 2 mm or more. In the portable electrocardiograph 100B in this embodiment, the size of the electrode region ($L_{21} \times L_{22}$ in FIG. 17) is 30 mm×20 mm, the distance ($H_{21}$ in FIG. 16) between the main face of the electrode region and the main face of the non-electrode region is 0.5 mm, and the size of the electrode formation face ($L_{23} \times L_{24}$ in FIG. 17) is 62 mm×27 mm. The width of the non-electrode region extending from the border with the electrode region to the end of the electrode formation face ($D_{21}$ and $D_{22}$ in FIG. 17) is 16 mm in the longitudinal direction of the electrode formation face and is 3.5 mm in the transverse direction.

Around the positive electrode 120 on the left side face 107 of the housing 101, a plurality of projections 107b are provided. The projection 107b is a part functioning as an anti-slip so as not to cause a positional deviation of the positive electrode 120 on the surface of the body at the time of measurement.

Preferably, the projection 107b is formed so that its height is the same or lower than the main face of the electrode region positioned so as to be projected. In the portable electrocardiograph 100B in this embodiment, the height ($H_{22}$ in FIG. 16) of the projection is 0.5 mm.

By providing the contact face 121 with the body of the positive electrode 120 so as to be projected from the left side face 107 of the housing 101, the test subject can easily recognize the position of the positive electrode 120, so that the measurement position is easily specified. In this case, by providing a plurality of projections in the non-electrode region, the positional deviation between the positive electrode and the body at the time of measurement can be prevented, so that the contact between the contact face of the electrode and the body can be stably maintained.

Third Embodiment

First, the structure of a portable electrocardiograph 100C in a third embodiment will be described. The same reference numerals will be given to components similar to those in the foregoing first embodiment and their description will not be repeated here.

Figure 18:
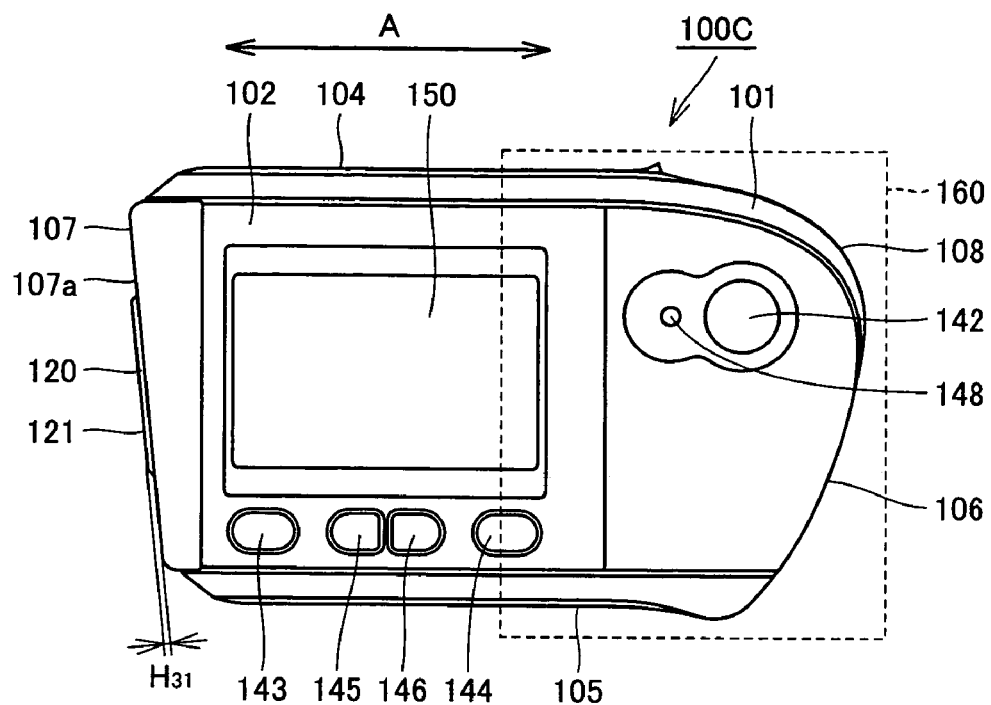
FIG. 18 is a front view of a portable electrocardiograph in a third embodiment of the present invention.
Figure 19:
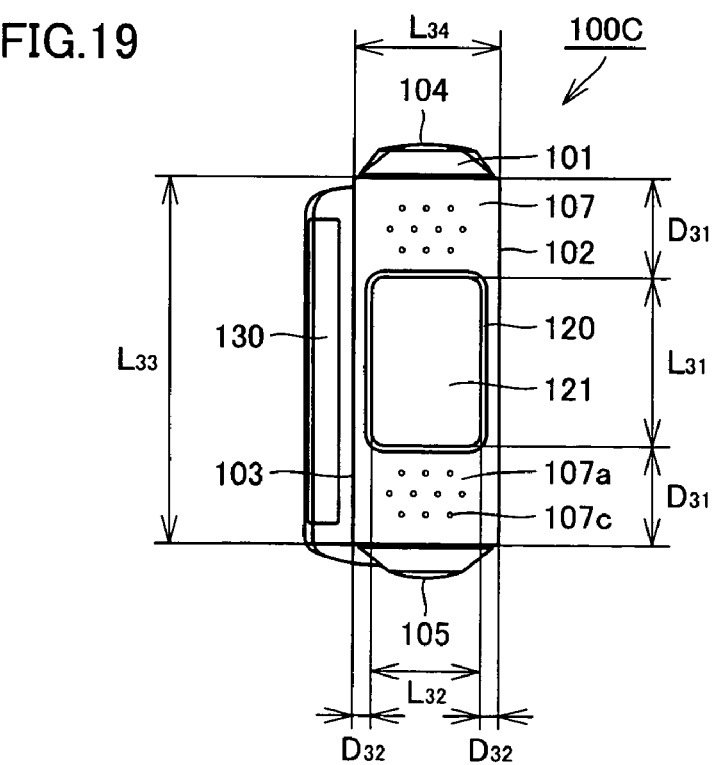
FIG. 19 is a left side view of the portable electrocardiograph in the third embodiment of the present invention.
Figure 20:
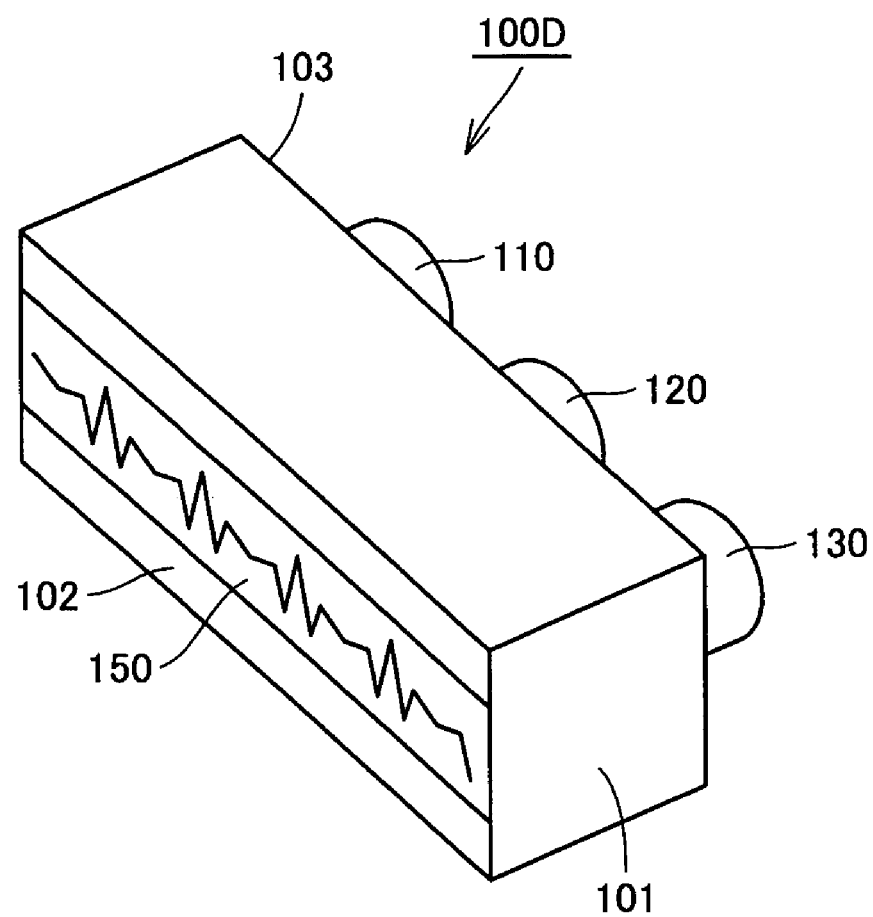
FIG. 20 is a perspective view showing an example of a conventional portable electrocardiograph.
Figure 21A:
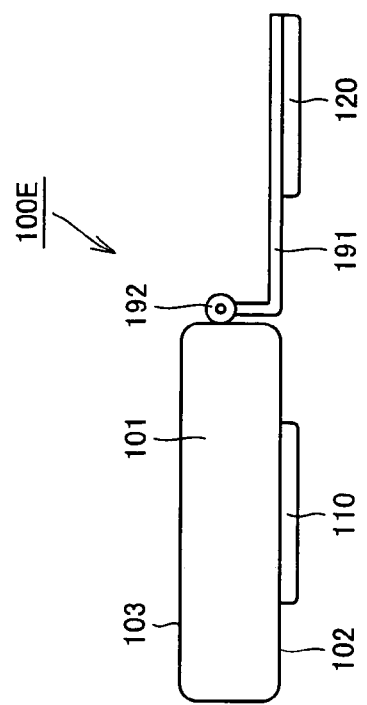
FIG. 21A is a front view showing another example of the conventional portable electrocardiograph.
Figure 21B:
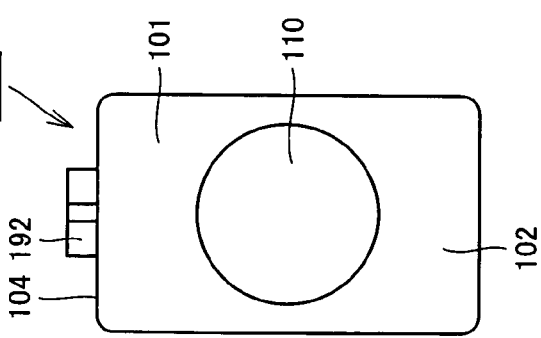
FIG. 21B is a left side view showing the conventional portable electrocardiograph illustrated in FIG. 21A.
Figure 21C:
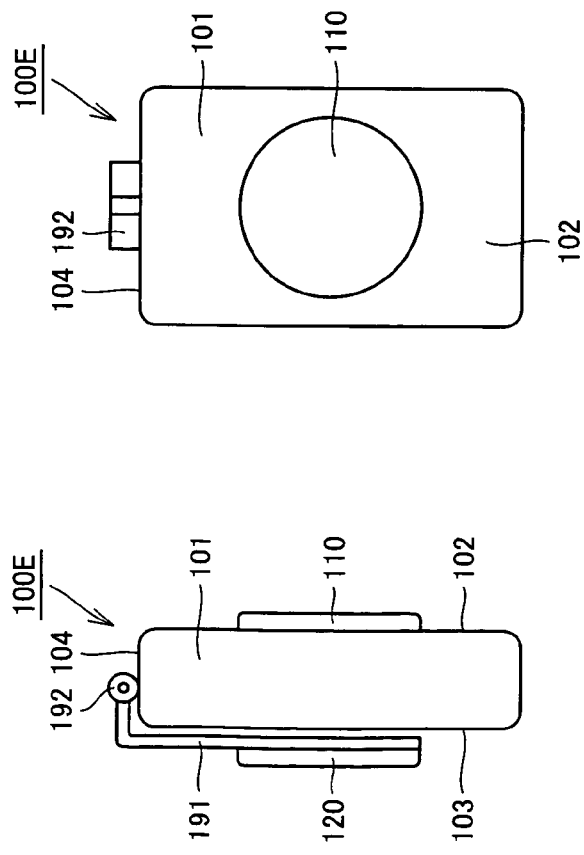
FIG. 21C is a left side view showing a state where the conventional portable electrocardiograph illustrated in FIG. 21A is open.
Figure 22A:
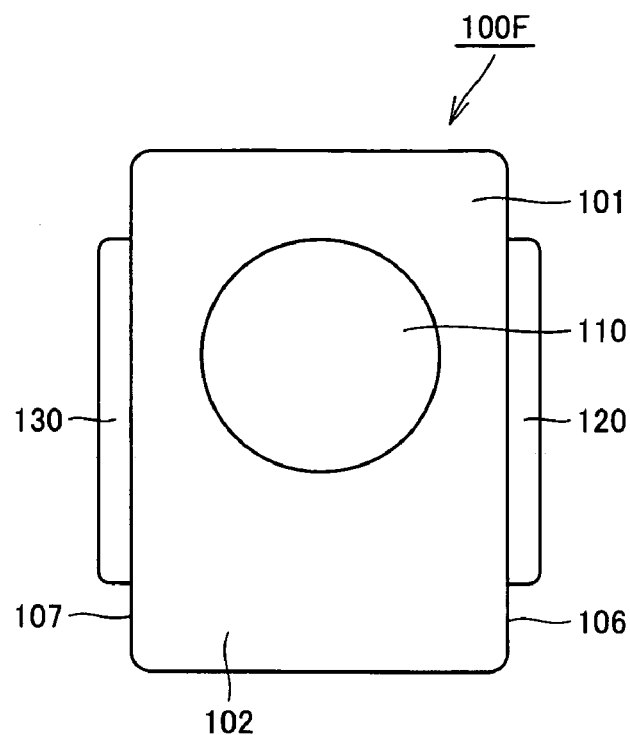
FIG. 22A is a front view showing still another example of the conventional portable electrocardiograph.
Figure 22B:
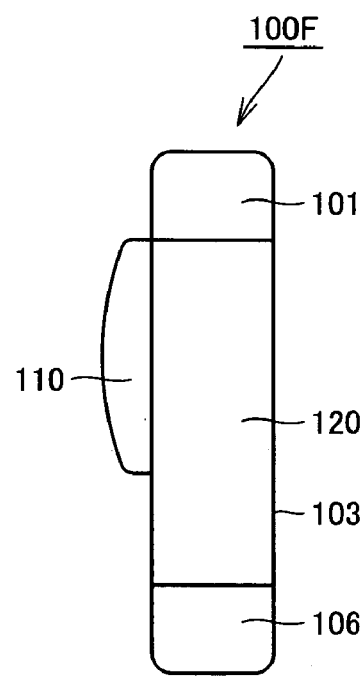
FIG. 22B is a right side view of the conventional portable electrocardiograph illustrated in FIG. 22A.
Figure 23:
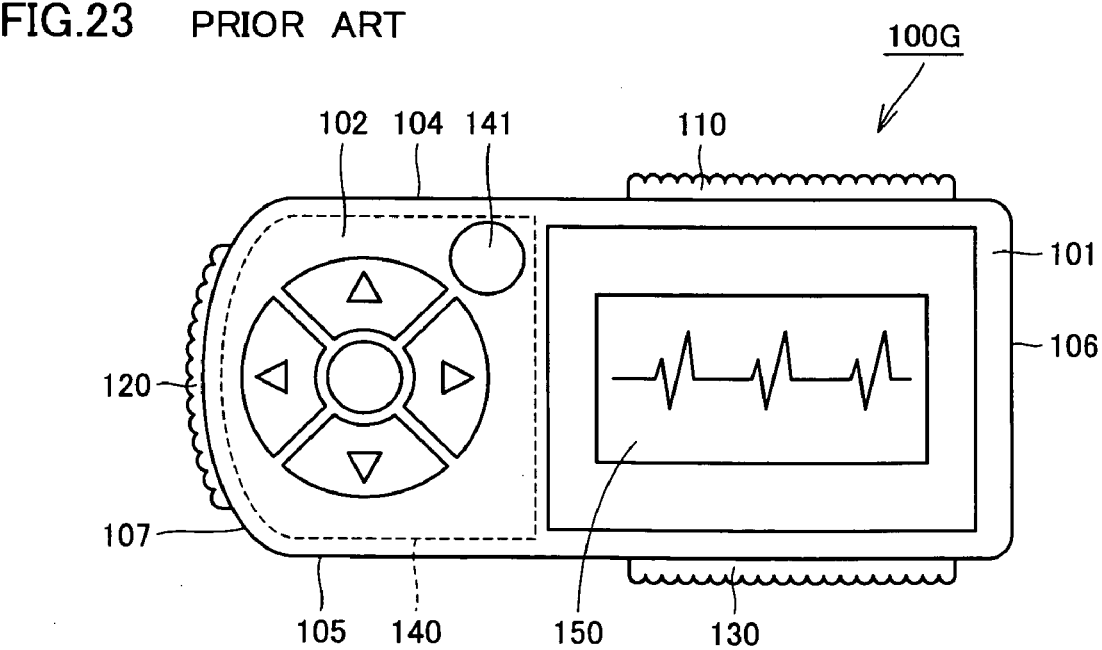
FIG. 23 is a front view showing yet another example of the conventional portable electrocardiograph.
Figure 24:
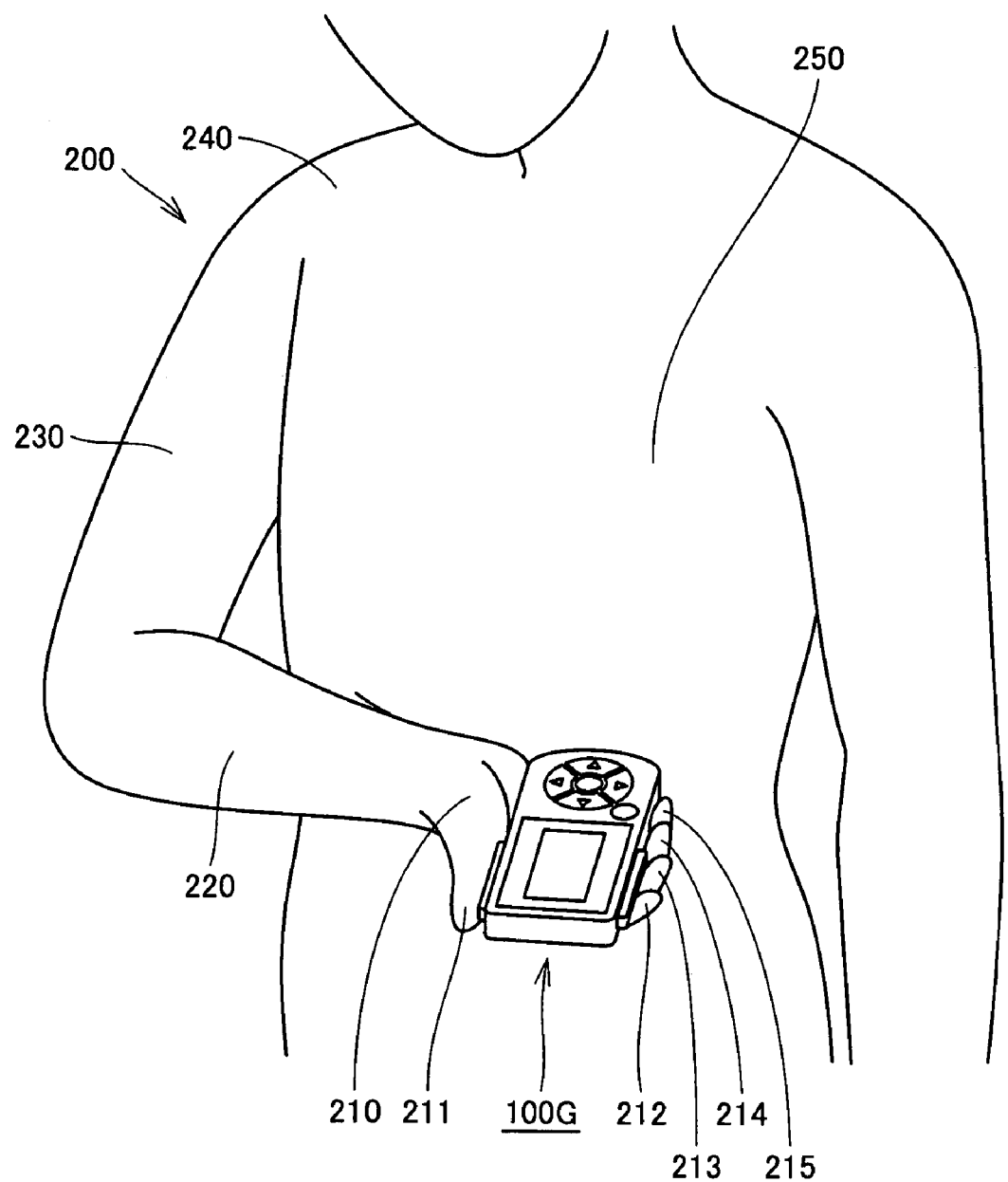
FIG. 24 is a diagram showing a measurement posture to be taken by the test subject at the time of measuring electrocardiographic waveforms by using the conventional portable electrocardiograph illustrated in FIG. 23.
Figure 25:
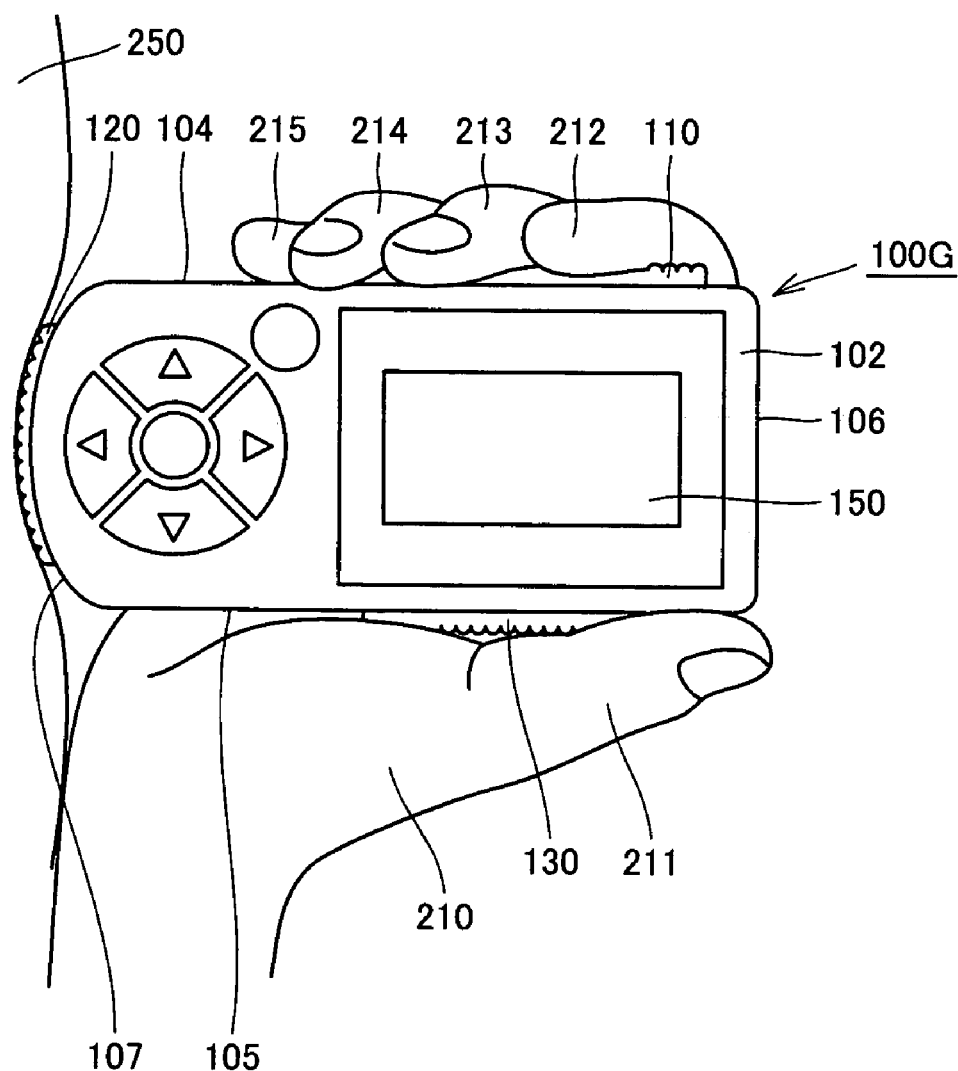
FIG. 25 is a diagram showing a state where the conventional portable electrocardiograph illustrated in FIG. 23 is held by the right hand to measure electrocardiographic waveforms.

As shown in FIGS. 18 and 19, the portable electrocardiograph 100C in this embodiment is different from the portable electrocardiograph 100A in the first embodiment only with respect to the structure of the left side face 107 as the electrode formation face of the housing 101.

The portable electrocardiograph 100C in this embodiment has the positive electrode 120 as the second electrode on the left side face 107 of the housing 101. The positive electrode 120 is made of an electroconductive material and is positioned at the center portion of the left side face 107 of the housing 101. Around the positive electrode 120, the flat face 107a made of an insulating material is formed. The contact face 121 with the body as the main face of the positive electrode 120 is provided so as to be projected from the main face of the flat face 107a. The contact face 121 of the positive electrode 120 is formed to be flat.

Specifically, the left side face 107 of the housing 101 as an electrode formation face is constructed by an electrode region in which the positive electrode 120 is positioned (i.e., the contact face 121 of the positive electrode 120) and a non-electrode region (i.e., the flat face 107a) positioned so as to surround the electrode region and formed to be flat. The main face of the electrode region is provided so as to be projected from the main face of the non-electrode region.

The contact face 121 of the positive electrode 120 has an almost rectangle shape and, preferably, the length of one side of the contact face 121 lies in the range from 20 mm to 30 mm. The distance between the main face of the electrode region positioned so as to be projected from the main face of the non-electrode region and the main face of the non-electrode region is preferably 1 mm or less. The width of the non-electrode region extending from the border with the electrode region to the end of the electrode formation face is, preferably, at least 2 mm or more. In the portable electrocardiograph 100C in this embodiment, the size of the electrode region ($L_{31} \times L_{32}$ in FIG. 19) is 30 mm×20 mm, the distance ($H_{31}$ in FIG. 18) between the main face of the electrode region and the main face of the non-electrode region is 0.5 mm, and the size of the electrode formation face ($L_{33} \times L_{34}$ in FIG. 19) is 62 mm×27 mm. The width of the non-electrode region extending from the border with the electrode region to the end of the electrode formation face ($D_{31}$ and $D_{32}$ in FIG. 19) is 16 mm in the longitudinal direction of the electrode formation face and is 3.5 mm in the transverse direction.

Around the positive electrode 120 on the left side face 107 of the housing 101, a plurality of recesses 107c are provided.

The recess 107c is a part functioning as an anti-slip so as not to cause a positional deviation of the positive electrode 120 on the surface of the body at the time of measurement.

The depth of the recess 107c is preferably 0.3 mm to 1 mm. In the portable electrocardiograph 100C in this embodiment, the depth of the recess is 0.5 mm.

By providing the contact face 121 with the body of the positive electrode 120 so as to be projected from the left side face 107 of the housing 101, the test subject can easily recognize the position of the positive electrode 120, so that the measurement position is easily specified. In this case, by providing a plurality of recesses in the non-electrode region, the positional deviation between the positive electrode and the body at the time of measurement can be prevented, so that the contact between the contact face of the electrode and the body can be stably maintained.

Although the foregoing first to third embodiments have been described by using, as examples, the portable electrocardiographs each constructed so that the grip region includes a first end face positioned adjacent to one end in the longitudinal direction of the housing, the present invention is not limited to the portable electrocardiographs having such a structure. Naturally, the present invention can be also applied to a portable electrocardiograph having a structure in which the grip region does not include a first end face, that is, a portable electrocardiograph intended to have a gripped state such that the one end face is not covered with the right hand.

Although the foregoing first to third embodiments have been described by using, as examples, the portable electrocardiographs each having three electrodes of the positive electrode, the negative electrode and the neutral electrode, the neutral electrode is not an essential electrode. The present invention can be applied to any portable electrocardiograph as long as it has a pair of measurement electrodes of at least a positive electrode and a negative electrode on the outer surface of the housing.

Further, although the foregoing first to third embodiments have been described by using, as examples, the portable electrocardiographs each having the display in the outer surface of the housing, the present invention can be naturally also applied to a portable electrocardiograph having a separately provided display. It is considered that a portable electrocardiograph having a separately provided display outputs measured electrocardiographic waveforms to an external display by radio or by wire.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A portable electrocardiograph for measuring electrocardiographic waveforms, comprising:
 a housing having a substantially rectangular parallelepiped shape and including,
  a grip region positioned on one end of the housing perpendicular to a longitudinal direction of the housing, said grip region gripped by a subject in measurement, and
  an end face positioned at another end of the housing perpendicular to the longitudinal direction of the housing, the end face pressed against a body surface and the grip region gripped by a hand;
 a first electrode provided in said grip region; and
 a second electrode provided on-said end face; wherein said end face includes an electrode region at which said second electrode is positioned and a non-electrode region positioned so as to surround said electrode region and formed to be flat wherein said non-electrode region is provided with a plurality of projections, and wherein, in operation, said electrode region and said non-electrode region are pressed against the body surface.

2. The portable electrocardiograph according to claim 1, wherein
said electrode region is positioned at a center portion of said end face.

3. The portable electrocardiograph according to claim 1, wherein
a main face of said electrode region is formed to be flat.

4. The portable electrocardiograph according to claim 3, wherein
the main face of said electrode region is flush with a main face of said non-electrode region.

5. The portable electrocardiograph according to claim 1, wherein
a main face said electrode region is positioned so as to be projected from a main face of said non-electrode region.

6. The portable electrocardiograph according to claim 5, wherein
a distance between an apex of each of said plurality of projections and the main face of said non-electrode region is equal to or shorter than a distance between the main face of said electrode region and the main face of said non-electrode region.

7. A portable electrocardiograph for measuring electrocardiographic waveforms, comprising:
a housing having a substantially rectangular parallelepiped shape and including,
a grip region positioned on one end of the housing perpendicular to a longitudinal direction of the housing, said grip region gripped by a subject in measurement, and
an end face positioned at another end of the housing perpendicular to the longitudinal direction of the housing, the end face pressed against a body surface and the grip region gripped by a hand;
a first electrode provided in said grip region; and
a second electrode provided on said end face; wherein
said end face includes an electrode region at which said second electrode is positioned and a non-electrode region positioned so as to surround said electrode region and formed to be flat, and wherein said non-electrode region is provided with a plurality of recesses, and wherein, in operation, both the electrode region and non-electrode region are pressed against the body surface.

8. The portable electrocardiograph according to claim 7, wherein said electrode region is positioned at a center potion of said end face.

9. The portable electrocardiograph according to claim 7, wherein a main face of said electrode region is formed to be flat.

10. The portable electrocardiograph according to claim 9, wherein the main face of said electrode region is flush with a main face of said non-electrode region.

11. The portable electrocardiograph according to claim 7, wherein
a main face of said electrode region is positioned so as to be projected from a main face of said non-electrode region.

* * * * *